United States Patent [19]

Kawahara

[11] Patent Number: 4,667,522
[45] Date of Patent: May 26, 1987

[54] HUMIDITY TESTING APPARATUS

[75] Inventor: Masaru Kawahara, Saitama, Japan

[73] Assignee: Express Test Corporation, Sunnyvale, Calif.

[21] Appl. No.: 794,192

[22] Filed: Nov. 1, 1985

[51] Int. Cl.$^4$ ............ G01N 25/00; G01N 33/00; G01N 17/00

[52] U.S. Cl. ............ 73/865.6; 374/57; 219/401

[58] Field of Search ............ 73/432 SD, 865.6; 374/57, 45, 208; 422/11, 26; 219/390, 401

[56] References Cited

U.S. PATENT DOCUMENTS

| | | | |
|---|---|---|---|
| 2,523,322 | 9/1950 | Ornstein et al. | 374/57 |
| 2,766,624 | 10/1956 | Heffner | 73/432 SD |
| 3,488,681 | 1/1970 | Mita et al. | 73/432 SD X |
| 3,886,791 | 6/1975 | Grossman | 73/432 SD X |
| 4,571,093 | 2/1986 | Gottlieb | 374/57 |

FOREIGN PATENT DOCUMENTS 838531 6/1981 U.S.S.R. ............ 374/57

Primary Examiner—Tom Noland
Attorney, Agent, or Firm—William B. Walker

[57] ABSTRACT

This invention is a humidity testing apparatus comprising a test chamber with external heaters for superheating the steam and preventing condensation in the testing zone. The test chamber is divided into an upper humidity testing section and lower condensate collection and removal section by a horizontal heating plate extending from the back wall to a front edge adjacent to and spaced apart from the front of the test chamber, the heating plate extending from one sidewall to the opposing sidewall of the chamber. Convection currents are introduced into the chamber by the heating plate which is maintained at a temperature above the walls of the chamber. The test chamber has a steam inlet opening in the back wall thereof defining a steam flow path into the upper chamber, and a substantially vertical steam baffle plate extending upward from the heating plate and positioned adjacent to the steam inlet opening in the steam flow path. The bottom wall has a condensate outlet opening in the bottom wall thereof.

4 Claims, 3 Drawing Figures

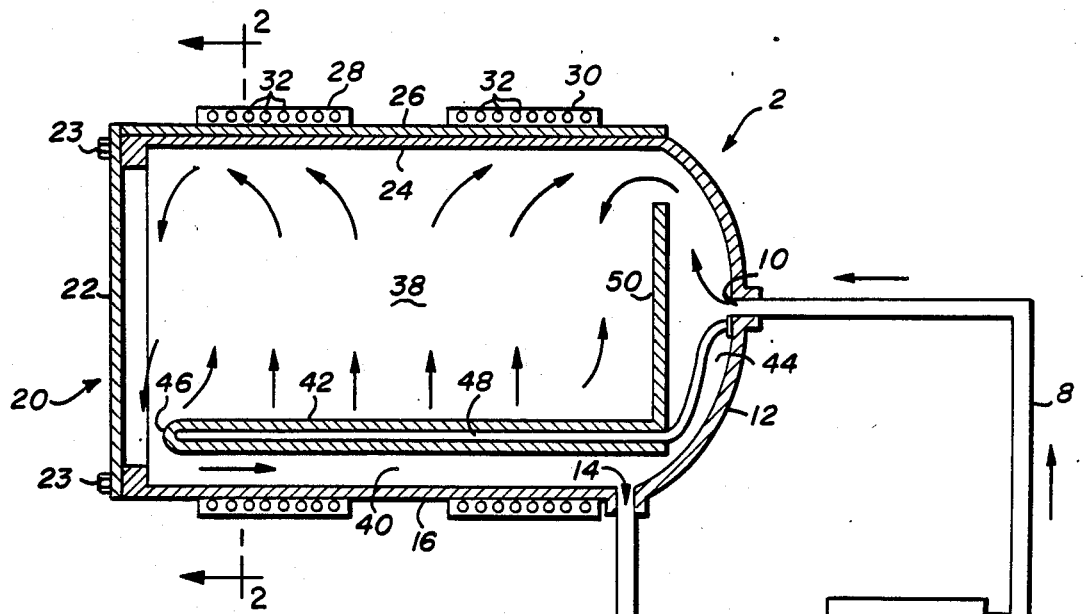
Fig_1
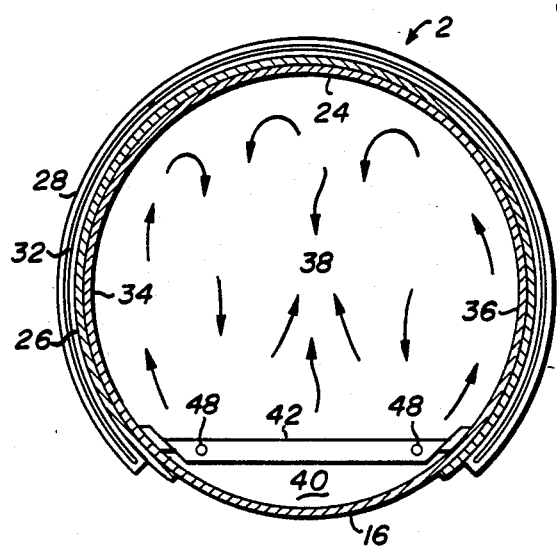
Fig_2
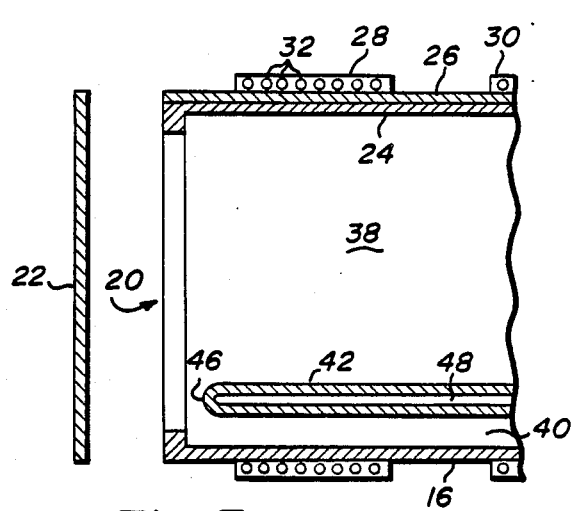
Fig_3

HUMIDITY TESTING APPARATUS

FIELD OF THE INVENTION

This invention relates to a humidity testing device. In particular, this invention relates to variable humidity testing apparatus for environmental testing of microelectronic circuits, assemblies using such circuits and other materials which may be exposed to potentially damaging environments.

BACKGROUND OF THE INVENTION

Environmental testing of electronic components and assemblies is routinely required for manufactured products which might be affected by environmental conditions. The ability to withstand wide ranges of environmental humidities and temperatures is critical for many electronic products, and proof of resistance to high humidities at elevated temperatures is often required by many industrial and military consumers. The object of this invention is to provide an improved humidity testing apparatus, in particularly a device with a more uniform and controllable environmental testing temperature and humidity.

DESCRIPTION OF THE PRIOR ART

Humidity chambers supplied with steam from external steam generators have been previously known. The temperature inside the chamber should be maintained at a level greater than the temperature of the entering steam to prevent condensation in the chamber, and to create an unsaturated humidity environment. This is usually achieved by placing auxiliary heating elements around the exterior of the humidity chamber.

SUMMARY OF THE INVENTION

This invention is a humidity testing apparatus comprising a test chamber for receiving items to be tested. The test chamber has a front; a top wall, a back wall, opposed side walls and a bottom wall; and an auxiliary heating means external to the test chamber for heating at least one outer wall of the test chamber. The test chamber is divided into an upper humidity testing section and lower condensate collection and removal section by a horizontal heating plate extending from the back wall to a front edge adjacent to and spaced apart from the front of the test chamber, the heating plate extending from one sidewall to the opposing sidewall of the chamber. The front of the test chamber comprises a loading and unloading opening for inserting items to be tested and a closure means for closing the loading and unloading opening. The test chamber has a steam inlet opening in the back wall thereof defining a steam flow path into the upper chamber, and a substantially vertical steam baffle plate extending upward from the heating plate and positioned adjacent to the steam inlet opening in the steam flow path. The bottom wall has a condensate outlet opening in the bottom wall thereof.

BRIEF DESCRIPTION OF THE DRAWINGS

FIG. 1 is a schematic cross-sectional view of a humidity test apparatus showing the chamber front in the closed position according to this invention.

FIG. 2 is a cross-sectional schematic view of the humidity test apparatus taken along the line 2—2 in FIG. 1.

FIG. 3 is a fragmentary cross-sectional view of the humidity test apparatus of FIG. 1 showing the chamber front in the open position.

DETAILED DESCRIPTION OF THE INVENTION

Referring to FIGS. 1 and 2, the humidity test chamber 2 is supplied with steam from the steam generator 4. Steam generated by the immersion heat coil 6 is delivered through conduit 8 to the steam inlet opening 10 in the back wall 12 of the test chamber. Condensate is drained through the outlet opening 14 in the bottom wall 16 of the test chamber and returned by conduit 18 to the steam generator.

The front 20 of the humidity test chamber 2 is an opening for loading and unloading devices to be tested. Closure 22 seals the opening in the front 20 and is designed to be securely fastened to the front of the vessel by conventional fastening means such as by bolts 23, for example. Because the steam is superheated in the vessel, the fasteners and outer walls of the humidity test chamber 2 must be sufficiently strong to withstand the elevated pressure. FIG. 3 shows the humidity test apparatus with the front 20 of chamber 38 in the open position with the front closure 23 removed.

The humidity test chamber 2 has an upper wall 24, back wall 12 and bottom wall 16. A heat conducting plate 26 and external heaters 28 and 30 with resistance heating elements 32 extend over the upper wall 24 and sidewalls 34 and 36 (FIG. 2).

The interior of the humidity chamber is divided into an upper humidity testing section 38 and lower condensate collection and removal section 40 by a horizontal heating plate 42. The heating plate 42 is attached to the sidewalls 34 and 36 (FIG. 2). Resistance heating elements are provided in the heating plate 42, the resistance heating elements portion 46 extending from the back wall 12 to the resistance heating element portion 48 enclosed by the heating plate 42.

A substantially vertical steam baffle plate 50 is supported mounted on and extends upward from the heating plate 42. The steam baffle plate 50 is positioned in the path of the entering steam entering though inlet opening 10, deflecting the steam flow, and preventing the entrance of entrained water droplets with the steam.

Referring to FIG. 2, the heating plate 42 extends from side wall 34 to side wall 36 of the humidity chamber and is mounted thereon.

The immersion heating coil 6 in the steam generator 4 produces steam which is passed by conduit 8 through the inlet opening 10 of the humidity chamber 2. The steam is deflected upward and sideways by the baffle 50 and enters the chamber along the walls 14, 34 and 36. External heaters 28 and 30 outside the test chamber 2 heat the conduction plate 26, raising the temperature of the walls 34, 24 and 36 to a temperature which is above the temperature of the steam entering the chamber through the inlet opening 10. Any droplets entrained in the steam is thus vaporized, and condensation of the vapor along the upper and sidewalls of the chamber is prevented. This heating coil arrangement produces a relative humidity condition within the upper test chamber below full saturation by the water vapor. In normal operation, the heating coils in the heaters 28 and 30 are energized before steam is introduced into the test chamber to minimize the risk of condensation in the upper testing section.

This invention is based on the discovery that even though the external heating coils provided an even heat distribution and prevented condensation in the test section of the chamber, stratification of vapors having different temperatures (and relative humidities) occurred because the gas convection was insufficient. The temperature in the upper portion of the upper testing chamber was typically higher than the lower portions. It was discovered that this deficiency could be overcome by providing a heated horizontal plate 42. Plate 42 provides a further function of supporting the devices being tested. In one convenient way of operating the apparatus of this invention, the devices being tested are mounted on open wire racks (not shown) which can be placed upon and be supported in the test chamber by the horizontal heating plate 42.

As the vapor in the upper testing section 38 is heated by the upper surface of the horizontal heating plate 42, it rises and is displaced by cooler gases, creating convection currents which mix the gases in the upper section 38. Convection being introduced, the gas temperatures and humidities throughout the upper section 38 are more uniform, stratified layers being disrupted and dispersed.

Vapor condensation in this configuration is limited to wall surfaces of the vessel below the heating plate 38 in the lower steam condensate section 40. The heated plate 42 supports devices being tested above the condensate zone. The accumulating condensate collects on the bottom of the lower chamber 40, flows through outlet 14 and is returned to the steam generator 4 through return conduit 18.

In a typical operation of the humidity testing device of this invention, steam is generated having a temperature of 120° C. and introduced through inlet opening 10. The steam, having an initial relative humidity of 100% is further heated by the walls 34, 24 and 36, which have a preset temperature of 125° C., for example. The vapor temperature increases to a temperature above 120° C., lowering the relative humidity to a level below 100%, preventing any condensation in the testing section 38.

The temperature of the heating plate 42 is preset to 130° C., for example. Vapors contacting the surface of the heating plate 42 is heated to a higher temperature than other gases and rise, creating and maintaining the convection flow of vapors in the test chamber.

This invention has been described with the use of external resistance heaters 28 and 30. Other types and configurations of internal and external heaters providing the same or an equivalent function can be used and are intended to be included in this invention. For example, an oven, infrared lamps, and induction heating devices and combinations of these with each other or with resistance heaters can be used to heat the external walls 34, 24 and 36.

I claim:

1. A humidity testing apparatus comprising a test chamber having a front, a top wall, a back wall, opposed side walls and a bottom wall, an auxiliary heating means external to the top wall and sidewalls for heating at least one outer wall of the test chamber, the test chamber is divided into an upper humidity testing section and lower condensate collection and removal section by a horizontal heating plate extending from the back wall to a front edge adjacent to and spaced apart from the front of the test chamber and extending from one sidewall to the opposing sidewall of the chamber.

2. The humidity testing apparatus of claim 1 wherein the front of the test chamber comprises a loading and unloading opening for inserting items to be tested, and a closure means is mounted on the front of the test chamber for closing the loading and unloading opening.

3. The humidity testing apparatus of claim 1 wherein the test chamber has a steam inlet opening in the back wall thereof defining a steam flow path into the upper chamber, and a substantially vertical steam baffle plate extends upward from the heating plate, positioned adjacent to the steam inlet opening in the steam flow path.

4. The humidity testing apparatus of claim 1 wherein the bottom wall has a condensate outlet opening therein.

* * * * *